(12) United States Patent
Schultz et al.

(10) Patent No.: US 11,834,389 B2
(45) Date of Patent: Dec. 5, 2023

(54) SYNTHESIS OF N-(2,4-DINITROPHENYL)-4-NITROBENZAMIDE (TNBA) USING SOLID ACID CATALYSTS

(71) Applicant: DUPONT SAFETY & CONSTRUCTION, INC., Wilmington, DE (US)

(72) Inventors: James A. Schultz, Swedesboro, NJ (US); Sourav Kumar Sengupta, Wilmington, DE (US); Venkateswara Rao Surisetty, Moseley, VA (US)

(73) Assignee: DUPONT SAFETY & CONSTRUCTION, INC., Wilmington, DE (US)

( * ) Notice: Subject to any disclaimer, the term of this patent is extended or adjusted under 35 U.S.C. 154(b) by 298 days.

(21) Appl. No.: 17/323,349

(22) Filed: May 18, 2021

(65) Prior Publication Data

US 2021/0387942 A1 Dec. 16, 2021

Related U.S. Application Data

(60) Provisional application No. 63/037,834, filed on Jun. 11, 2020.

(51) Int. Cl.
| | |
|---|---|
| *C07C 231/14* | (2006.01) |
| *B01J 8/02* | (2006.01) |
| *B01J 19/14* | (2006.01) |
| *B01J 21/16* | (2006.01) |
| *B01J 29/70* | (2006.01) |
| *B01J 39/20* | (2006.01) |

(52) U.S. Cl.
CPC ............... *C07C 231/14* (2013.01); *B01J 8/02* (2013.01); *B01J 19/14* (2013.01); *B01J 21/16* (2013.01); *B01J 29/7007* (2013.01); *B01J 39/20* (2013.01); *B01J 2219/00051* (2013.01)

(58) Field of Classification Search
None
See application file for complete search history.

(56) References Cited

U.S. PATENT DOCUMENTS

| | | | |
|---|---|---|---|
| 2,366,007 | A | 12/1944 | Gaetano |
| 2,500,149 | A | 3/1950 | Boyer |

FOREIGN PATENT DOCUMENTS

| | | |
|---|---|---|
| RU | 2283307 C1 | 9/2006 |
| RU | 2394810 C2 | 7/2010 |
| RU | 2547262 C3 | 4/2015 |

OTHER PUBLICATIONS

Sun et al. (Tetrahedron, 2009, 65, 3480). (Year: 2009).*
PCT International Search Report for International Application No. PCT/US2021/036296; Stefania Tabanella, Authorized Officer; ISA/EPO; Aug. 31, 2021.
Sun Y et al., "Colorimetric detection of Cyanide with N-nitrophenyl benzamide derivatives", Tetrahedron Elsevier Publishers, vol. 65, No. 17, Apr. 25, 2009.

* cited by examiner

*Primary Examiner* — Sudhakar Katakam
*Assistant Examiner* — Jennifer C Sawyer

(57) ABSTRACT

A method of making N-(2,4-dinitrophenyl)-4-nitrobenzamide from a mixture of 2,4-dinitroaniline, 4-nitrobenzoyl chloride, and solid acid catalyst in an organic solvent, wherein the solid acid catalyst is not soluble in the organic solvent, the solid acid catalyst being an acidic clay, an ion exchange resin, a beta zeolite, a sulfonated tetrafluoroethylene-based fluoropolymer-copolymer, or some mixture of these.

17 Claims, 1 Drawing Sheet

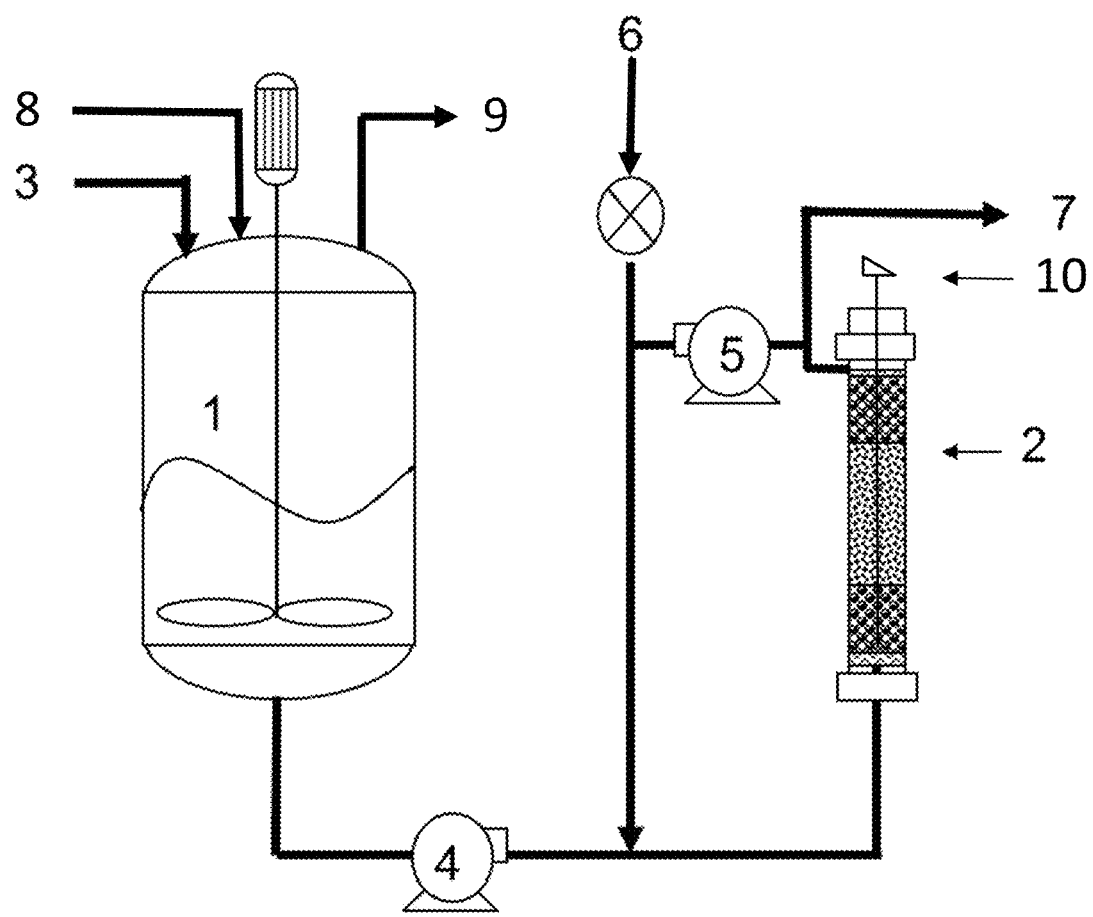

SYNTHESIS OF N-(2,4-DINITROPHENYL)-4-NITROBENZAMIDE (TNBA) USING SOLID ACID CATALYSTS

BACKGROUND OF THE INVENTION

Field of the Invention

This invention relates to an improved method of making N-(2,4-dinitrophenyl)-4-nitrobenzamide (TN BA) from 2,4-dinitroaniline (2,4-DNA) and 4-nitrobenzoyl chloride (4-NBC).

Description of Related Art

RU2283307(C1) discloses a method for synthesis of 5(6)-amino-2-(4'-aminophenyl) benzimidazole from N-(2,4-dinitrophenyl)-4-nitrobenzamide. The method for making the N-(2,4-dinitrophenyl)-4-nitrobenzamide involves an acylation reaction of 2,4-dinitroaniline and 4-nitrobenzoyl chloride in the presence of ferric chloride as a catalyst in a solvent medium chosen from chlorobenzene, paraxylene, or a mixture of xylenes, toluene or ethylbenzene, which is said to form 2,4',4-trinitrobenzanilide, which is the same as N-(2,4-dinitrophenyl)-4-nitrobenzamide. The reaction is conducted at an elevated temperature, and once it is essentially complete, the solution is cooled, resulting in the precipitation of TNBA from the solvent medium. The TNBA is then washed with fresh solvent medium and subsequently with water to yield the desired TNBA. Other publications such as RU2394810(C2) and RU2547262(C3) disclose similar processes for making TNBA in the presence of an iron chloride catalyst.

It has been found that the ferric (iron) chloride catalyst poses a problem in that it is soluble in the solvent medium, meaning that both the solvent system and the precipitate TNBA produced by this process will contain the catalyst as an undesirable impurity that must further be removed. Specifically, the preferred method of removing the catalyst from the TNBA, such as disclosed in RU2283307(C1), is to first isolate the TNBA from the solvent system and then further wash the TNBA with copious amounts of water to remove the catalyst. Furthermore, if the TNBA produced by the above prior art process is subsequently used in other catalyzed reactions, any residual ferric (iron) chloride present in the TNBA can poison any downstream catalyst(s) and/or impart color to the final product. In addition, the ferric chloride catalyst used in the above prior art process cannot be recycled and reused, and its use represents a substantial disposal problem, increasing the operating cost of the manufacturing process.

What is needed is a process that avoids all the issues associated with the use of catalysts that are soluble in the organic solvent system and that also allows process design flexibility to either precipitate the TNBA from the solvent system or use the TNBA dissolved in the solvent system in further processing.

BRIEF SUMMARY OF THE INVENTION

This invention also relates to a method of making N-(2, 4-dinitrophenyl)-4-nitrobenzamide (TNBA), a monomer useful in the manufacture of advanced polymers.

In some embodiments, this invention relates to a method of making N-(2,4-dinitrophenyl)-4-nitrobenzamide comprising the steps of:

a) forming a first mixture comprising 2,4-dinitroaniline and 4-nitrobenzoyl chloride in an organic solvent;

b) reacting the first mixture at a temperature of at least 90° C. in the presence of a solid acid catalyst, wherein the solid acid catalyst is not soluble in the organic solvent, to form a second mixture comprising N-(2,4-dinitrophenyl)-4-nitrobenzamide and the organic solvent, wherein the solid acid catalyst is an acidic clay, an ion exchange resin, a beta zeolite, a sulfonated tetrafluoroethylene-based fluoropolymer-copolymer, or some mixture thereof;

c) cooling the second mixture to precipitate the N-(2,4-dinitrophenyl)-4-nitrobenzamide as a solid; and d) removing the solid N-(2,4-dinitrophenyl)-4-nitrobenzamide from the second mixture.

BRIEF DESCRIPTION OF THE DRAWINGS

FIG. 1 illustrates one continuous method for making N-(2,4-dinitrophenyl)-4-nitrobenzamide) (TNBA).

DETAILED DESCRIPTION OF THE INVENTION

This invention relates to a method of making N-(2,4-dinitrophenyl)-4-nitrobenzamide from a mixture of 2,4-dinitroaniline, 4-nitrobenzoyl chloride, and solid acid catalyst in an organic solvent, wherein the solid acid catalyst is not soluble in the organic solvent. This is an improvement over processes that utilize catalysts such as iron chloride ($FeCl_3$) that are soluble in organic solvents; when such soluble catalysts are used, it can contaminate the final reaction product and is difficult to remove from the reaction media. Soluble catalysts such as iron chloride ($FeCl_3$) have traditionally been used because they are inexpensive and such homogenous catalytic reactions of a Lewis acid type are known to be useful in this reaction.

The solid acid catalysts that are both suitable for the desired reaction and are insoluble in the organic solvent used for the reaction include acidic clays, ion exchange resins, beta zeolites, sulfonated tetrafluoroethylene-based fluoropolymer-copolymers, and mixtures of these catalysts. It was a surprise to the inventors that a heterogeneous catalytic reaction using a Bronsted-type catalyst would be effective with this reaction.

The method of making N-(2,4-dinitrophenyl)-4-nitrobenzamide (TNBA) from a mixture of 2,4-dinitroaniline (2,4-DNA), 4-nitrobenzoyl chloride (4-NBC), and solid acid catalyst in an organic solvent can be achieved either via a batch process, a semi-batch or stepwise process, or a continuous process. For example, the mixture of 2,4-DNA and 4-NBC in a solvent can be reacted to form TNBA in the presence of a catalyst in a continuous process that utilizes a fixed bed or packed bed catalytic reactor (essentially a vessel with immobilized catalyst packed therein) that does not require any agitation. Alternatively, batch, semi-batch, or continuous slurry processes can be used to react the 2,4-DNA and 4-NBC in a solvent to form TNBA in the presence of a catalyst using equipment such as mechanically stirred autoclave, continuously stirred tank reactor (CSTR) or gas agitated reactors such as a slurry bubble column reactor (SBCR).

The claimed reaction is carried out in a solvent, preferably under an inert atmosphere. A suitable organic solvent is an aromatic solvent in which 2,4-DNA, 4-NBC, and desired product TNBA are soluble, at a temperature of 60° C. or greater. Preferably, the boiling point of the solvent at atmospheric pressure is greater than 100° C., more preferably greater than 120° C., and most preferably greater than 140° C. Further, it is preferred that the solvent can be dried azeotropically.

In some embodiments, suitable organic solvents include xylenes, toluene, chlorobenzene, o-dichlorobenzene, and trichlorobenzene, or mixtures thereof; with preferred organic solvents being chlorobenzene and o-dichlorobenzene, or mixtures thereof. In some embodiments, the preferred organic solvent is chlorobenzene.

For good yield of the reaction, the 2,4-DNA should be dry. This means the 2,4-DNA preferably contains less than 500 ppm of water on a weight basis; and more preferably contains less than 200 ppm of water on a weight basis. Likewise, the 4-NBC should also be dry, preferably containing less than 500 ppm of water on a weight basis; and more preferably contains less than 200 ppm of water on a weight basis.

Further, impurities in the ingredients can lower the yield and can affect the purity of the resulting product mixture. Therefore, it is desirable that both the 2,4-DNA and the 4-NBC have a purity of at least 90%, preferably a 95% purity, and more preferably a purity of greater than 99%. Specifically, it is preferable that the 4-NBC be substantially free of organic impurities, containing less than 0.5 weight percent 4-nitrobenzoic acid (4-NBA).

The mixture further comprises a solid acid catalyst that is not soluble in the organic solvent. By "not soluble in the organic solvent" it is meant there is no difference between the elemental analysis of a reaction mixture containing the catalyst and the same reaction mixture not containing the catalyst, or any such difference is within experimental error of the instrument. Specifically, there is no difference between the elemental analysis of (1) the mixture containing 2,4-dinitroaniline, 4-nitrobenzoyl chloride, and solid acid catalyst in the organic solvent and (2) the mixture containing only 2,4-dinitroaniline, 4-nitrobenzoyl chloride, and the organic solvent, or any such difference is within experimental error of the instrument.

A catalyst is a substance that modifies the transition state of a reaction to a lower activation energy, increasing the rate of reaction. By "solid acid catalyst" it is meant catalysts that have protons or coordinately unsaturated cationic centers on their surface having the thermal stability required to survive reaction conditions and substantially undissolved in the reaction medium under the reaction conditions. The solid acid catalysts may be unsupported, or may be supported on at least one catalyst support.

The solid acid catalysts that are both suitable for the desired reaction and are insoluble in the organic solvent used for the reaction include acidic clays, ion exchange resins, beta zeolites, sulfonated tetrafluoroethylene-based fluoropolymer-copolymers, and mixtures of these catalysts.

In some embodiments, the preferred solid acid catalysts are natural acid clay minerals. Natural acidic clay minerals include kaolinite, bentonite, attapulgite, and montmorillonite. Montmorillonite is a preferred acidic clay.

Suitable ion-exchange resins are crosslinked copolymer particles (e.g. beads), that have been chemically treated to attach or form functional groups and have a capacity for ion exchange. In one embodiment, the ion-exchange resin comprises an aromatic polymer that further comprises crosslinked copolymers of styrene or substituted styrene and a crosslinker such as divinylbenzene. Further, such ion-exchange resins having sulfonic acid functional groups were found to be particularly active and selective. U.S. Pat. Nos. 2,366,007 and 2,500,149 describe the preparation of cation exchange resins based on such sulfonated styrene-divinylbenzene copolymers.

Suitable sulfonated tetrafluoroethylene-based fluoropolymer-copolymers include such things as Nafion® NR50.

In an embodiment, the solid acid catalyst is a supported acid catalyst. The support for the solid acid catalyst can be any solid substance that is inert under the reaction conditions including, but not limited to, oxides such as silica, alumina, titania, sulfated titania, and compounds thereof and combinations thereof; barium sulfate; calcium carbonate; zirconia; carbons, particularly acid washed carbon; and combinations thereof. Acid washed carbon is a carbon that has been washed with an acid, such as nitric acid, sulfuric acid or acetic acid, to remove impurities. The support can be in the form of powder, granules, pellets, or the like. The supported acid catalyst can be prepared by depositing the acid catalyst on the support by any number of methods such as spraying, soaking or physical mixing, followed by drying, calcination, and if necessary, activation through methods such as reduction or oxidation. The loading of the at least one acid catalyst on the at least one support is in the range of 0.1-20 weight percent based on the combined weights of the at least one acid catalyst and the at least one support. Certain acid catalysts perform better at low loadings such as 0.1-5%, whereas other acid catalysts are more likely to be useful at higher loadings such as 10-20%. In an embodiment, the acid catalyst is an unsupported catalyst having 100% acid catalyst with no support such as, pure beta zeolites and ion exchange resins.

Both the supported and unsupported solid acid catalyst can be in any physical form typical for the material, including but not limited to powdered forms, with 0.01-150 μm particle size. For fixed bed reactors, the catalyst is generally in the form of tablets, extrudates, spheres, and/or engineered particles, having a uniform 0.5-10 mm size.

The general method of making N-(2,4-dinitrophenyl)-4-nitrobenzamide comprises the steps of:
a) forming a first mixture comprising 2,4-dinitroaniline and 4-nitrobenzoyl chloride in an organic solvent;
b) reacting the first mixture at a temperature of at least 90° C. in the presence of a solid acid catalyst, wherein the solid acid catalyst is not soluble in the organic solvent, to form a second mixture comprising N-(2,4-dinitrophenyl)-4-nitrobenzamide and the organic solvent, wherein the solid acid catalyst is an acidic clay, an ion exchange resin, a beta zeolite, a sulfonated tetrafluoroethylene-based fluoropolymer-copolymer, or some mixture thereof;
c) cooling the second mixture to precipitate the N-(2,4-dinitrophenyl)-4-nitrobenzamide as a solid; and
d) removing the solid N-(2,4-dinitrophenyl)-4-nitrobenzamide from the second mixture.

In a continuous process, it can be advantageous to perform the mixing step a) and the reacting step b) in separate vessels, such as stirred tank for mixing and a fixed bed or packed bed catalytic reactor for reacting the ingredients. However, steps a) and b) can be performed in a single vessel if desired, conceivably in either a continuous process or a batch, semi-batch, or semi-continuous process. For example, the combination of steps a) and b) can be accomplished, in a batch method by forming a first mixture of the 2,4-DNA, 4-NBC, and the solid acid catalyst in an organic solvent and reacting this mixture, optionally with agitation, to form a second mixture comprising the TNBA, the solid acid catalyst, and the organic solvent, plus any unreacted 2,4-DNA and 4-NBC.

Preferably both steps a) and b), or the combined steps a) and b), are conducted in an inert atmosphere, such as under a nitrogen atmosphere. Preferably some sort of agitation is present in steps a) and b), either via mechanical stirring or the like, or static mixers, or even fluid dynamics, such as the turbulence that arises in the pumping of a mixture through a packed column or a slurry reactor.

While ideally equal molar amounts of 2,4-DNA and 4-NBC are needed for the reaction, generally an excess molar amount of 4-NBC is added to compensate for common impurities; 4-NBC is almost always contaminated with some amount of the corresponding acid PNBA. In some preferred embodiments, the molar ratio of 4-NBC to 2,4-DNA is 1.05 to 1.07. In addition, in some preferred embodiments, the first mixture is formed by mixing at least 50 grams of 2,4-DNA per liter of solvent, and in some embodiments mixing 200 grams or more of 2,4-DNA per liter of solvent is even more preferred.

If steps a) and b) are performed in a single vessel, conceivably using an unsupported catalyst, the catalyst is present in the first mixture in an amount that is generally at least 5 weight percent of the amount of 2,4-DNA present in the first mixture. Preferably the catalyst is present in the first mixture in an amount that is at least 20 weight percent of the amount of 2,4-DNA present in the first mixture, and more preferably in an amount that is at least 30 weight percent of the amount of 2,4-DNA present in the first mixture.

Various active steps can be taken to avoid moisture in the individual reactants and/or the first mixture. For example, the individual ingredients like the 2,4-DNA can be pre-dried (e.g., under vacuum; 85-100° C. in a vacuum oven using a small nitrogen bleed). In some process variants like a batch, semi-batch or step-wise reaction, the combination of the unsupported catalyst and the 2,4-DNA can be dried together in a solvent by sparging nitrogen and simultaneously heating the mixture in the reactor under reflux condition. However, if these mixtures are heated under reflux condition, it is desirable to cool the system to 120° C. or less prior to the introduction of the (4-NBC). Alternatively, a mixture of the 2,4-DNA, 4-NBC, and the organic solvent can be formed, followed by, or concurrent with, the removal of undesirable amounts of water in the mixture by heating or by some other known technique, prior to the catalyzed reaction. This dried mixture can then subsequently contact the solid acid catalyst for the catalyzed reaction to take place.

The catalyzed reaction of the first mixture forms a second mixture comprising at least the N-(2,4-dinitrophenyl)-4-nitrobenzamide (TNBA) in the organic solvent. It is advantageous to react the ingredients at a temperature of at least about 90° C. In some embodiments, it is advantageous to react the ingredients at a temperature of at least about 100° C. In some embodiments, the reaction temperature can range from about 90° C. to about 135° C. In some embodiments, the reaction temperature can range from about 100° C. to about 135° C. In some embodiments, the reaction temperature can range from about 100° C. to about 125° C. In some embodiments, the temperature can be ramped gradually from one level to another and held for a fixed period of time and this process can be continued several times until the final temperature is attained and held for a fixed period of time. For example, in a batch reaction the hold time can range from 0.5 to 10 hours, preferably between 0.5 to 7.5 hours, and more preferably from 0.5 to 5 hours. Preferably, byproduct hydrochloric acid gas that evolves from the reaction is swept from the reaction using the inert gas blanketing the reaction (typically nitrogen gas). Especially in a batch reaction, agitation is desired during the hold time and is continued until the reaction is completed or an adequate amount of TNBA is formed. The extent of reaction can be determined by the disappearance of 2,4-DNA, the limiting reactant, determined by analyzing a small portion of aliquot from the reaction mixture using thin layer chromatography (TLC) or high-performance liquid chromatography (HPLC).

If an unsupported solid acid catalyst is used for the reaction and is part of the TNBA product mixture along with the solvent, the solid acid catalyst can be removed by filtration, preferably by hot filtration. For example, TNBA has very high solubility in the solvent chlorobenzene at high temperatures, and very low solubility at low temperatures. Therefore, it is advantageous to remove the solid acid catalyst at high temperatures to avoid removing any of the desired TNBA. The mixture of TNBA and solvent can then be cooled to crystallize and precipitate solid TNBA, and then the TNBA can be separated from the solvent. Typically, this separation is accomplished by filtration. Preferably, the filtration is accomplished using a Rosenmund filter, Nutsche filter, filter press or rotary drum filter. Finally, the solid TNBA is washed and dried in vacuum oven. Specifically, the solid TNBA can be washed with an alcohol such as with methanol or otherwise treated to remove residual organic solvent. Likewise, if desired, the TNBA can be washed with a weak aqueous base, such as sodium hydroxide, to remove any acidic byproducts of the reaction, such as hydrochloric acid.

EXAMPLES

As used in the following examples, percent (%) conversion and percent yield are defined as:

$$\% \text{ Conversion} = \frac{(\text{mols of 2,4-DNA charged} - \text{mols of 2,4-DNA remaining})}{\text{mols 2,4-DNA charged}} \times 100$$

$$\% \text{ Yield} = \frac{\text{mols of } TNBA \text{ formed}}{\text{mols of 2,4-DNA charged}} \times 100$$

The amounts of TNBA, 4-NBC, and 2,4-DNA were determined using the area percent technique using HPLC chromatograms.

Comparative Example A and Examples 1-4

Comparative Example A and Examples 1 through 4 illustrate a batch method for making N-(2,4-dinitrophenyl)-4-nitrobenzamide) (TNBA). 15 grams (0.082 mol) of 2,4-dinitroaniline (2,4-DNA), dried overnight in vacuum oven at 100° C. under a small continuous bleed of nitrogen, 17.2 grams (0.092 mol) of 4-nitrobenzoyl chloride (4-NBC), 5.0 grams of the catalyst, and 200 ml of chlorobenzene were placed in a 500 ml four neck reaction flask fitted with a thermocouple, mechanical stirrer, nitrogen inlet, and a condenser. The reaction mixture was heated to 120° C. and stirred for desired reaction time. After the reaction was carried out for the time on stream reported in the Table below, it was cooled overnight to room temperature. Then, 100 ml of dimethylformamide was added in the reaction vessel, heated to 80° C. and stirred for 1 hour. The reaction mixture was filtered hot using 0.2μ fritted filter and the solution was analyzed by HPLC. The conversions of 2,4-DNA and the yields of n-(2,4-dinitrophenyl)-4-nitrobenzamide) (TNBA) for the different types of solid acid catalysts and times on stream have been delineated in the Table below.

TABLE 1

| Example | Catalyst | Time (hours) | Conversion (%) | Yield (%) |
|---|---|---|---|---|
| A | None | 12 | 94.6 | 92.7 |
| 1 | Montmorillonite Clay | 6 | 99.7 | 97.2 |
| 2 | CP-814E Beta Zeolite | 12 | 99.9 | 90.6 |
| 3 | Nafion ® NR50 | 8 | 85.9 | 84.6 |
| 4 | Dowex ® Marathon ™ CH+ | 10 | 99.8 | 98.2 |

Note:
Conversion and Yield based on HPLC area %.

A calculation of the rate of reaction in these Examples illustrates the rate of reaction in the absence of catalyst is the lowest, with the relative rates of reaction being as follows: No Catalyst (7.8 h−1)<CP-814E Beta Zeolite (8.3 h−1) <Dowex® Marathon™ CH+(10 h−1)<Nafion® NR 50 (10.7 h−1)<Montmorillonite clay (16.6 h−1).

Example 5

This example illustrates a stepwise method for making N-(2,4-dinitrophenyl)-4-nitrobenzamide) (TNBA). 30 grams (0.164 mol) of 2,4-dinitroaniline (2,4-DNA) and 200 ml of chlorobenzene were placed in a 1000 ml four neck reaction flask fitted with a thermometer, magnetic stir bar, nitrogen inlet and a Dean-Stark trap. The mixture was stirred for 5 minutes under a nitrogen atmosphere. The mixture was heated to reflux and 7 ml of chlorobenzene condensate was collected to help remove any residual moisture. 10 Grams of solid Montmorillonite (K-10) catalyst were added after the 7 ml of chlorobenzene condensate was recovered.

The solution temperature was cooled down to 120° C. and 32.1 grams (0.168 mol) of 4-nitrobenzoyl chloride (4-NBC) was added using a powder funnel. Once the 4-NBC addition was completed, the reaction mixture was heated to reflux and stirred for 5 hours. After cooling overnight to room temperature, a tan solid precipitated from solution. The solid was collected by filtration. The collected solid was washed in a beaker with 200 ml of methanol, filtered and washed with 500 ml water, which was adjusted to pH 7.0 with 0.1 N NaOH. The solids were recovered and dried in a vacuum oven at 100° C. overnight. The reaction yielded 51.56 grams of N-(2,4-dinitrophenyl)-4-nitrobenzamide) (TNBA) (94.7% yield based on 2,4-DNA). The TNBA weight was corrected for the weight of the Montmorillonite since it was not removed in this procedure.

Examples 6-8

15 grams (0.082 mol) of 2,4-dinitroaniline (2,4-DNA), dried overnight in vacuum oven at 100° C. under a small continuous bleed of nitrogen, a specified amount of catalyst as reported in the Table 2, and 100 ml of 1,2-dichlorobenzene were placed in a 500 mL four neck reaction flask fitted with a thermocouple, mechanical stirrer, addition funnel with a nitrogen inlet, and a condenser. The reaction mixture was heated to 120° C. and 17.2 grams (0.092 mol) of 4-nitrobenzoyl chloride (4-NBC) dissolved in 100 mL of 1,2-dichlorobenzene from the addition funnel was continuously added in 30 minutes under constant stirring. The reaction mixture was maintained at 120° C. and stirred for the desired reaction time. After the reaction was carried out for the time on stream reported in the Table below, it was cooled overnight to room temperature. Then, 100 ml of dimethylformamide was added in the reaction vessel, heated to 80° C. and stirred for 1 hour. The reaction mixture was filtered hot using 0.2μ fritted filter and the solution was analyzed by HPLC. The conversions of 2,4-DNA and the yields of N-(2,4-dinitrophenyl)-4-nitrobenzamide) (TNBA) for the different types of solid acid catalysts, amounts of catalysts, and time on stream have been delineated in the Table below.

TABLE 2

| Example | Catalyst | Amount of Catalyst (g) | Time (h) | Conversion (%) | Yield (%) |
|---|---|---|---|---|---|
| 6 | Montmorillonite Clay | 5 | 3 | 99.6 | 97.2 |
| 7 | FULCAT 22B | 5 | 3 | 98.0 | 96.2 |
| 8 | Montmorillonite Clay | 1 | 3 | 99.2 | 97.2 |

Note:
Conversion and yield based on HPLC area %.

Comparison Example B

Comparative Example B illustrates the prior art use of iron chloride catalyst, which is soluble in the solvent. The batch procedure of Examples 1 to 4 was used with FeCl₃ as the catalyst. Specifically, 68 mg of FeCl₃ catalyst was added, and the reaction was run for 2.5 hours. A 97.8% yield of TNBA was obtained for 99.6% conversion of 2,4-DNA (limiting reactant), which is comparable to the inventive examples; however, additional steps were needed to remove the FeCl₃ catalyst from the final product.

Typically, a process such as the following is necessary to remove iron chloride from the final product. After the complete conversion of 2,4DNA, TNBA wet cake is separated from mother liquor. The wet cake is first washed with methanol four times (~1.4×wt. of wet cake in each wash), followed by washing one time with an aqueous ammonium hydroxide wash with 0.25 wt % ammonia (~2.5×wt. of wet cake), and finally washed 2 times with demineralized water washes (2×wt. of wet cake in each wash).

Example 9

This example illustrates one continuous method for making N-(2,4-dinitrophenyl)-4-nitrobenzamide) (TNBA) as shown in FIG. 1. The process utilizes a mixing vessel 1 and a fixed bed catalytic reactor 2 containing a solid acid catalyst. Reactants 2,4-DNA and 4-NBC and solvent chlorobenzene are introduced into the mixing vessel 1 via an entry point 3, where they are mixed. The mixing vessel 1 is inerted using nitrogen introduced through entry point 8 and purged out of the vessel through exit point 9. The mixture of 2,4-DNA and 4-NBC in chlorobenzene is pumped to the catalytic reactor 2 via a pump 4. The catalytic reactor is fitted with a multipoint thermocouple 10 to maintain and control the temperature in the catalyst bed. The desired TNBA generated in the fixed bed reactor in the organic solvent exits the process via exit 7. A part of the exit stream from the fixed bed reactor is recycled back into the process via pump 5. The catalytic reactor 2 is provided with nitrogen via entry point 6. In this arrangement, the nitrogen is supplied into a recycle stream via the recycle line, but it can be supplied directly to the catalytic reactor if desired.

What is claimed is:

1. A method of making N-(2,4-dinitrophenyl)-4-nitrobenzamide comprising the steps of:
   a) forming a first mixture comprising 2,4-dinitroaniline and 4-nitrobenzoyl chloride in an organic solvent;
   b) reacting the first mixture at a temperature of at least 90° C. in the presence of a solid acid catalyst, wherein the solid acid catalyst is not soluble in the organic solvent, to form a second mixture comprising N-(2,4-dinitrophenyl)-4-nitrobenzamide and the organic solvent,
      wherein the solid acid catalyst is an acidic clay, an ion exchange resin, a beta zeolite, a sulfonated tetrafluoroethylene-based fluoropolymer-copolymer, or some mixture thereof;
   c) cooling the second mixture to precipitate the N-(2,4-dinitrophenyl)-4-nitrobenzamide as a solid; and
   d) removing the solid N-(2,4-dinitrophenyl)-4-nitrobenzamide from the second mixture.

2. The method of claim 1 wherein the first mixture comprising 2,4-dinitroaniline and 4-nitrobenzoyl chloride in an organic solvent formed in a) includes the solid acid catalyst.

3. The method of claim 2 wherein the first mixture including the solid acid catalyst is formed by premixing the 2,4-dinitroaniline, organic solvent, and solid acid catalyst and subsequently adding 4-nitrobenzoyl chloride.

4. The method of claim 1 wherein the solid acid catalyst is part of a continuous fixed bed reactor.

5. The method of claim 2 wherein step b) includes agitating the first mixture.

6. The method of claim 2 wherein after step b) but prior to step c) the solid acid catalyst is removed from the second mixture.

7. The method of claim 6 wherein the solid acid catalyst is removed by filtration.

8. The method of claim 1 wherein the acidic clay is a montmorillonite clay.

9. The method of claim 1 wherein the ion exchange resin is an ion-exchange resin having sulfonic acid functional groups.

10. The method of claim 1 wherein at least step b) is conducted under an inert atmosphere.

11. The method of claim 1 wherein prior to step a) the 2,4-dinitroaniline is combined with organic solvent and moisture is removed from the combination.

12. The method of claim 1 wherein the organic solvent is chlorobenzene.

13. The method of claim 1 wherein the solid N-(2,4-dinitrophenyl)-4-nitrobenzamide is removed in step d) by filtration.

14. The method of claim 1 wherein step a) is conducted at a temperature of about 100° C. to about 135° C.

15. The method of claim 3 wherein step b) includes agitating the first mixture.

16. The method of claim 3 wherein after step b) but prior to step c) the solid acid catalyst is removed from the second mixture.

17. The method of claim 16 wherein the solid acid catalyst is removed by filtration.

* * * * *